(12) United States Patent  
Lorch (10) Patent No.: US 7,281,541 B2
(45) Date of Patent: Oct. 16, 2007

(54) DENTAL FLOSS

(76) Inventor: Leonard G. Lorch, 118 Baltimore Ave. Lower Unit, Larkspur, CA (US) 94939

( * ) Notice: Subject to any disclaimer, the term of this patent is extended or adjusted under 35 U.S.C. 154(b) by 332 days.

(21) Appl. No.: 10/870,249

(22) Filed: Jun. 16, 2004

(65) Prior Publication Data

US 2005/0279378 A1 Dec. 22, 2005

(51) Int. Cl.
*A61C 15/00* (2006.01)
(52) U.S. Cl. .................................. 132/321
(58) Field of Classification Search .......... 132/321, 132/329; 424/439, 440; 426/134, 104, 135, 426/282, 132
See application file for complete search history.

(56) References Cited

U.S. PATENT DOCUMENTS

| | | | |
|---|---|---|---|
| 718,401 A | 1/1903 | Thomas | |
| 1,637,153 A | 7/1927 | Lawton | |
| 1,929,906 A | * 10/1933 | Skokowski | 426/272 |
| 2,771,889 A | 11/1956 | Fleming | |
| 3,754,332 A | 8/1973 | Warren | |
| 3,860,013 A | 1/1975 | Czapor | |
| 3,869,555 A | * 3/1975 | Heonis | 426/134 |
| 3,966,055 A | * 6/1976 | Francavilla | 211/65 |
| 4,162,687 A | 7/1979 | Lorch | |
| 4,270,556 A | 6/1981 | McAllister | |
| 4,450,849 A | 5/1984 | Cerceo et al. | |
| 4,776,358 A | 10/1988 | Lorch | |
| 4,974,615 A | 12/1990 | Doundoulakis | |
| 4,998,978 A | 3/1991 | Varum | |
| 5,033,488 A | 7/1991 | Curtis et al. | |
| 5,209,251 A | 5/1993 | Curtis et al. | |
| 5,220,932 A | 6/1993 | Blass | |
| 5,407,623 A | 4/1995 | Zacharides et al. | |
| 5,479,952 A | 1/1996 | Zachariades et al. | |
| 5,503,842 A | 4/1996 | Fazan et al. | |

(Continued)

FOREIGN PATENT DOCUMENTS

WO   WO 00/42992   7/2000

OTHER PUBLICATIONS

Libby Wiersema, Listerine might trump flossing in war against tooth decay, morningnewsonline.com, Jun. 15, 2004, http://www.morningnewsonlne.com/servlet/satellite?pagename=FMN%2FMGArticle%2FF MN_BasicArticle& c=MG Article & cid=1031776057536& path=, The Morning News, Florence, USA.

(Continued)

*Primary Examiner*—Todd E. Manahan
(74) *Attorney, Agent, or Firm*—Donn K. Harms (57) ABSTRACT

An improved dental floss employing a planar substrate with one or a plurality of apertures formed therein. At each aperture, a pair of edible substrate side portions having a perimeter portion slightly larger than the perimeter of the aperture are positioned and joined to each other through the aperture in the planar substrate thereby securing the edible substrate to the planar substrate. Dismounting of the edible substrate is achieved by tensioning the planar substrate around a tooth during use and aided by saliva dissolving the edible substrate. The edible substrate can be flavored or impregnated with medicine, mouthwash or flavorings. Additionally at least one of the two side portions of the edible substrate may include a design element which may include a geometric shape, a cartoon shape, indicia, or a logo.

20 Claims, 3 Drawing Sheets

U.S. PATENT DOCUMENTS

| | | | |
|---|---|---|---|
| 5,518,012 | A | 5/1996 | Dolan et al. |
| 5,578,373 | A | 11/1996 | Kobayashi |
| D382,668 | S | 8/1997 | Dolan |
| 5,765,576 | A | 6/1998 | Dolan et al. |
| 5,800,823 | A | 9/1998 | Blass |
| 5,806,539 | A | 9/1998 | Blass et al. |
| 5,819,768 | A | 10/1998 | Bible et al. |
| 5,897,895 | A * | 4/1999 | Bongiovanni ................. 426/91 |
| 5,908,039 | A | 6/1999 | Ochs et al. |
| 5,911,228 | A | 6/1999 | Curtis et al. |
| 5,973,290 | A | 10/1999 | Noddin |
| 6,080,481 | A | 6/2000 | Ochs et al. |
| 6,161,555 | A | 12/2000 | Chen |
| 6,220,256 | B1 | 4/2001 | Dolan et al. |
| 6,398,093 | B1 | 6/2002 | Dolan |
| 6,495,179 | B1 | 12/2002 | Zeitlow et al. |
| 6,539,951 | B2 | 4/2003 | Baillie et al. |
| 6,552,024 | B1 | 4/2003 | Chen et al. |
| 6,596,298 | B2 | 7/2003 | Leung et al. |
| 6,609,527 | B2 | 8/2003 | Brown |
| 6,651,676 | B1 | 11/2003 | Hekimian |
| 6,656,493 | B2 | 12/2003 | Dzija et al. |
| 6,709,526 | B1 | 3/2004 | Bailey et al. |
| 6,740,332 | B2 | 5/2004 | Zyck et al. |
| 6,743,388 | B2 | 6/2004 | Sridharan et al. |
| 6,766,808 | B2 | 7/2004 | Gwen |
| 7,055,530 | B2 * | 6/2006 | Husted ........................ 132/321 |
| 2002/0104548 | A1 | 8/2002 | Bhupendra |
| 2003/0178044 | A1 | 9/2003 | Brown et al. |
| 2003/0224090 | A1 | 12/2003 | Pearce et al. |
| 2003/0235630 | A1 | 12/2003 | Nussen |
| 2004/0003827 | A1 | 1/2004 | Gwen |
| 2004/0036193 | A1 | 2/2004 | Berry et al. |
| 2004/0043134 | A1 | 3/2004 | Corriveau et al. |
| 2004/0048231 | A1 * | 3/2004 | Perlin ......................... 434/263 |
| 2004/0081713 | A1 | 4/2004 | Maxwell et al. |
| 2004/0087467 | A1 | 5/2004 | MacQuarrie |
| 2004/0096569 | A1 | 5/2004 | Barkalow et al. |
| 2004/0111275 | A1 | 6/2004 | Kroll et al. |
| 2004/0163664 | A1 | 8/2004 | Husted |

OTHER PUBLICATIONS

Leonard G. Lorch, Safeguarded Flossing Device, Quintessence International, Apr. 1981, 415-417, vol. 12, No. 4, Quintessence Publishing Inc., Chicago, USA.

Steven T. Bunn, How to Floss, drbunn.com, (c) 2000-2004 Last updated May 22, 2004, drbunn.com/flossing.htm, Steven T. Bunn, D.D.S, Alexandria, USA.

* cited by examiner

DENTAL FLOSS

BACKGROUND OF THE INVENTION

1. Field of the Invention

The present invention relates to dental floss. More particularly the device and method herein disclosed relates to a device which may be used in an ongoing dental hygiene regime for flossing and is particularly suited to train an individual in the proper techniques of dental flossing while concurrently encouraging such flossing through the provision of a taste as well as visual reward system. This reward to the user is provided by a tasty dissolving substrate material communicating through apertures formed through the planar flossing substrate which are adapted for an interlocked engagement therethrough and calculated release therefrom during use.

By providing a substantially planar flossing substrate comprised of a material having a low coefficient of friction, the floss user in an ongoing regimen of flossing or the new user in training, is provided with a flossing material substantially easier to grip than conventional dental floss and which also glides through the narrow gaps between adjacent teeth with relative ease.

Proper use of such a planar floss is temporally encouraged by the immediate provision of the good taste of the releasable dissolving substrate material which provides ongoing positive reinforcement to the user during regular flossing or for the duration of the floss training exercise. Further, the dissolvable substrate can be used to freshen breath. Still further, additional encouragement can be provided by forming the dissolving substrate into the shape of cartoons or other whimsical characters that a child or young adult would find amusing during their temporary appearance in the mouth. Additionally, in the case where a specific manufacturer has a well known logo, the dissolving substrate could be formed in the shape of the logo and/or bearing the manufacturer's name. This embodiment would be especially useful to dentifrice manufacturers who wish to advertise their names on the flossing material itself and would allow temporary imparting of the name and/or logo of the manufacturer right onto the teeth of the user while the dissolving substrate is in the mouth.

2. Prior Art

The use of dental floss is recommended by virtually all dental health practitioners, for example dental professionals like dentists and dental hygienists. Dental flossing has been shown to be effective in removing interdental plaque according to the American Dental Association's Council on Scientific Affairs. Despite these facts, U.S. patent application 20020104548 (Bhupendra of Johnson & Johnson) indicates only about 12% of the United States population use floss regularly (that is, daily).

Modern dentistry has established that the use of dental floss and other interdental cleaners are an important part of dental hygiene and required daily to remove plaque and other particulate from between the teeth and under the gum line. These are the areas in the mouth which a toothbrush cannot reach and frequent initiation sites for tooth decay if they are not cleaned regularly. While most people should be taught when they are children about the proper manner and frequency of flossing, if older children or adults have not properly learned this hygienic art, it is never too late to start.

When flossing properly, a user is required to gently ease conventional thread-like floss between the teeth and gum line. In adjacent teeth that have positive contact, passing the round thread-like conventional floss therebetween can be a daunting task due to the frictional resistance of the adjacent tooth's side edges. Conventionally, about an 18 inch strand of floss is used in such regimens.

In use, holding both ends of a piece of floss for proper flossing dictates that the user form a "C" against the individual sides of two adjacent teeth and thereafter gently rub or slide the floss up and down the side edge of the tooth being cleaned. Holding the floss in this manner and moving it from under the gum line to the top of the tooth helps remove harmful plaque. As with any procedure for ongoing hygiene, it is important for the user to establish a regular pattern of flossing and remember to floss the backside of the last teeth.

Unfortunately, with children and many adults there is an inherent problem with the very thread-like nature of dental floss being hard to hold in their uncoordinated hands. Training can thus be very frustrating to the child and even cause eventual frustration to an adult attempting to learn the art of flossing. Additionally, in using conventional dental floss there is no positive reinforcement advanced to the child or young adult during training other than perhaps oral encouragement from the instructor. Without the instructor present, the user attempting self-instruction with dental floss will generally become discouraged over their inability to hold onto the thread-like ends, and the lack of any positive reinforcement for doing so. Further, as frequently occurs with experienced users of thread-like floss, the distal ends of the floss being used can have a tendency to painfully "strangle" the fingers around which they are wrapped. The result of these deterrents to flossing use and practice is frequently a failure in the instruction of new users to proper dental flossing and a resulting failure of their flossing hygiene program before it event starts. Even in ongoing users in a flossing regimen, such inconveniences can be a resulting cause of reduced flossing. Attempts to rectify some of these hindrances and design flaws have been advanced by some prior art.

U.S. Pat. No. 3,754,332 (Warren) teaches a preferably metal treatment member which incorporates a section of the member for the delivery of medication between the teeth which may be detached. The preferred embodiment employs an aperture which adjoins one edge of the member. Adhesive is preferably used to adhere an absorbent material about the edge of the aperture. In use the member containing the absorbent section is worked between the teeth to place the absorbent section, impregnated with fluoride or other medicine, in a position to transfer the medicine to the teeth. It can then impart the medicine to the teeth while the member is disposed therebetween. Or, as noted in Warren, the absorbent section, especially if placed on an edge, can be made to break the adhesive bond holding it to the member to leave it in place between the teeth. However, the absorbent material covering the apertures in Warren require an adhesive to maintain the absorbent material in place on the member. This use of an adhesive can limit the material used for the member due to adherence issues, and can make detachment complicated should the adhesive fail to release the absorbent material from its bond to one surface of the member.

U.S. Pat. No. 4,270,556 (McAllister) teaches the use of a prophylaxis strip (for example made of stainless steel) for professionally altering or cleaning interproximal surfaces and contact areas between teeth. The strip contains longitudinal perforations with each perforation preferably having a raised, peripheral scaling edge. However, McAllister lacks any teaching or suggestion of engaging a dissolvable film through the apertures in a mount which will encourage the user to continue flossing and a continued use of a metal strip with raised ridges over a long period of use could have adverse affects on the tooth enamel and irritate gums.

U.S. Pat. No. 4,776,358 (Lorch) teaches the benefits derived from an improved dental flossing material in the form of a tape preferably formed of expanded polytetrafluoroethylene (PTFE) folded longitudinally to form a pair of laminae defining a recess therebetween in which an abrasive or non-abrasive cleaning material is disposed. During the cleaning procedure, material flows from the free edges of the tape to become deposited upon the surfaces of the teeth and adjacent gingiva. However, while being an excellent teaching of the benefits of the use of a planar style floss, Lorch lacks any teaching or suggestion for the provision of a dissolvable film engaged through apertures in the tape to provide positive reinforcement and breath freshening to the user.

As such, there is an unmet need for device that may be employed for flossing by users in an ongoing regimen of flossing that is capable of excellent cleaning of the teeth while concurrently providing a taste or visual reward to the user. Such a flossing component, in the case of small children, young adults, and any dental patients being introduced to proper flossing technique, should provide for a flossing device that will be easy for users to grasp in their hands and not painful when wrapped tightly around fingers. Further, such a floss device should provide easy traverse through the narrow gaps between adjacent teeth, and concurrently be gentle on the gums during use thus encouraging practice as well as ongoing use. Such a flossing device should also be easily viewed during such use to provide the new user a means to gauge their physical actions during both use and practice giving a clear view of the movement of the floss material on tooth surfaces during regular or practice flossing sessions. Still further, such a floss device should avail itself to easy and repeated use in a flossing regimen or for self-instruction, while concurrently temporally coupling some sort of ongoing positive reinforcement to be enjoyed by the user during the flossing session to thereby encourage continuation of such flossing activity. Additionally, such a flossing device should provide the ability to form logos, cartoons, or indicia, in the dissolvable substrate to provide encouragement for use or advertising of the manufacturer. Finally, such a floss should be able to provide for breath freshening in addition to the provision of a pleasant taste for ongoing positive reinforcement.

SUMMARY OF THE INVENTION

The device and method herein disclosed and described achieves the above-mentioned goals of optimum floss use and practicing by providing a floss device which can be easily employed by children and other new users to flossing, as well as being employed by adults tired of the negative aspects of a thread type floss.

In all preferred embodiments a planar flossing substrate material is provided due to its ease of traverse between gaps in the teeth and ease of handling by the fingers without resulting strangulation. Such a planar substrate also provides excellent cleaning ability when engaged upon and slid up or down the side surface of a tooth.

The planar flossing material employs a plurality of individual apertures formed in the material which communicate between the first and second side surfaces of the planar flossing material. The individual apertures have a circumference which is sized slightly smaller than the area of a pair of edible and dissolvable substrates which are placed in registered engagement over the individual apertures. These two dissolving substrates so placed are then adhered to each other through the aperture in the substrate which is thereby sandwiched therebetween. The result is that the two sections of edible substrate are engaged upon the planar flossing substrate since they are joined through the aperture and both have respective perimeters slightly larger than the perimeter of the aperture between them.

Further, the two substrates are not adhered or glued to the planar flossing substrate itself but engaged therethrough rendering them removable easily under tension or after a defined period in the mouth dissolves the bond holding them together. So long as the circumference of both edible substrates are slightly larger than the circumference of the aperture through which they are joined, or one dimension of both edible substrates is wide enough to overhang two opposing sides of the aperture, the edible substrates will stay mounted in position on the planar flossing substrate. Adhering only the two substrates to each other and not to the planar substrate defines a notch or recess about the perimeter of the two edible substrates to surround portions of planar substrate adjacent to the aperture perimeter edge. This mounting is maintained as long as they are attached to each other at their respective center sections and through the aperture using a means to adhere one edible substrate to the other.

By joining two opposing edible substrate portions through the apertures in the planar flossing substrate to mount them thereto, a wide variety of shapes and sizes of the edible substrates may be used. The shape of the edible substrate does not necessarily have to mirror that of the aperture, it just has to have at a minimum at least one side edge of each edible substrate portion project over two side edges of the aperture to maintain it in position. Of course more projections are preferred for the preferred stable mount in the aperture but not adhered to the planar substrate adjacent to the aperture.

The shape therefore can vary from simple shaped edible substrates substantially the same shape as the aperture, to decorative shaped substrates or cartoon character shaped substrates or virtually any shape desired so long as two side edges of both substrates are at least slightly larger than the distance between two opposing edges of the aperture. Or, in another preferred embodiment, which would have special appeal to floss suppliers, the shape of the edible substrate might be that of the logo of the manufacturer or could carry indicia of the brand name of the floss. Or, the edible substrate can be any of an infinite number of designs such as that of the logo or name of a sports team or city, or just about any desired design. This would provide an excellent means of advertising to the floss supplier and would be desirable when used on the end product or on samples handed out at dental offices and trade shows to encourage use of the vending manufacturer's product later on. It would be especially desirable for the rabid sports fan to temporarily adhere his team's logo and colors to their smile. In such cases where extended viewing of the detached edible substrate on the teeth of the user might be desirable, using a material that is slow to dissolve and tends to stick to the tooth would be desirable. To that end, including a means to slow dissolution of the edible substrate, for example gelatin comprising at least 50% of the edible substrate by weight, will enable the edible substrate to adhere to the user's tooth during the dissolving period which is lengthened thereby effectively decorating the tooth with the team logo, cartoon, or geometric shape, or making the tooth a billboard for the logo or manufacturer's indica.

Consequently, it is envisioned that whimsical shaped edible substrates such as cartoons or star shaped, or other fun shaped edible substrates might be employed where some sort of visual encouragement is desired for the user such as a child. It is further anticipated that the edible substrates could be engaged on the floss substrate and bear the indicia in the form of the name and/or logo of the manufacturer of the product, a team logo, city or geographic designs, or any design appropriate to the purpose can be employed.

The apertures formed through the flossing substrate can be die cut, laser cut, or formed by any conventional means to remove a section of the flossing substrate to form the appropriately shaped and sized aperture to accommodate the pair of edible substrates to be engaged therethrough. The edible substrates similarly can be die cut, laser cut, molded, or formed in any conventional fashion which will enable the appropriately shaped and sized edible substrates to engage through the formed aperture and thereby mount to the flossing substrate. As will be obvious to those skilled in the art, the disclosed device if sold commercially would be manufactured in great quantity. As is the case with such devices, specialized machinery can be manufactured to form the various components in the correct sizes and to assemble them into the finished product. All such manufacturing improvements to yield the device are anticipated.

A favored material for forming the flossing substrate would be PTFE substantially one-half inch wide however those skilled in the art will realize that other materials suitable to the task and in other sizes can be used and such are anticipated in the scope of this patent. A plurality of apertures are formed in the flossing substrate with a current preferred shape of the aperture being an ellipse preferably of isometric form. The apertures would be formed on substantially four inch centers however any spacing can be used and is anticipated. Any planar substrate that is both edible and dissolves when exposed to liquid, especially saliva, may be formed into the two edible planar substrate portions which are joined at their respective center portions through the aperture to hold them both in place on the flossing substrate.

A current preferred edible film would be Listerine RTM oral care strips available from Pfizer or Flash Strips available from Wrigley or a similar material which will dissolve in the mouth of the user when mounted on the flossing substrate and exposed to saliva thereby enabling dismounting of the edible film. This edible film forming the flossing substrate can contain one or a combination of mouthwash, medicine, flavoring, or special design elements, or any number of inducements for the use of the floss to clean or freshen the mouth. The edible film is also dismountable by forming the aperture in a shape to deform under a calculated amount of tension on the flossing substrate when the flossing substrate is manipulated around a tooth also dismounting the edible substrate by releasing the sandwich relationship between it and the two engaged pieces of edible film joined through the aperture. In cases where making the edible film stick to the tooth during the dissolving period is desirable, adding a means to slow the dissolution of the edible film, say for example the aforementioned gelatin to edible substrate at a rate of 50% by weight, tends to make it stick to the tooth for a longer duration as it dissolves.

Two pieces of the edible substrate, cut to the appropriate size and shape and/or bearing one or a combination of the appropriate design elements including a geometric shape, a cartoon shape, indicia or a logo, on at least one piece would then be joined together, at their center sections, through the aperture using a means to adhere one side section of edible substrate to the other. This could be accomplished by adhesive, or wetting the two substrates and bringing them into a sticky contact that is allowed to dry and adhere, or other means to adhere or engage one side section to the other. The edible substrate might also be formed in the shape of a rivet or ingot such that a smaller planar side edge connects to a larger planar side and mounting is accomplished by forcing the smaller planar side through the aperture which would stretch long enough to allow passage of the smaller planar side therethrough to capture the flossing substrate between the two planar sides. The flossing substrate with the edible substrate in registered engagement through the apertures would be provided to the user in long rolls from which sections may be removed for use, or in short sections, ready for use or in long rolls with pre-formed shorter frangible lengths that may be torn from the longer roll.

With respect to the above description, before explaining at least one preferred embodiment of the herein disclosed invention in detail, it is to be understood that the invention is not limited in its application to the details of construction and to the arrangement of the components or steps set forth in the method in the following description or illustrated in the drawings, nor just to children. The apparatus and methods of employing the invention herein are capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception, upon which this disclosure is based, may readily be utilized as a basis for designing of other structures, methods and systems for carrying out the several purposes of the present disclosed device and method. It is important, therefore, that the claims be regarded as including such equivalent construction and methodology insofar as they do not depart from the spirit and scope of the present invention.

It is an object of this invention to provide a dental floss device which provides the user with positive reinforcement during use to encourage such use.

It is an object of this invention to provide a dental floss device that also freshens breath.

It is another object of the invention to provide a dental article which visibly guides the user to partially and/or substantially knockout the breath freshening means.

It is an additional object of this invention to provide a dental article, which provides positive reinforcement for use, by employing a sweet or tasty substance which is removably engaged through the flossing substrate.

It is yet another object of the invention to provide a dental article which is simple, convenient for both student and accomplished floss user to employ.

It is an additional object of the present invention is to provide a dental article which is safe and comfortable to grab, non-slip and non binding on the fingers and subsequently easy to maneuver in the mouth of the user.

It is another object of the present invention to temporally couple the positive reinforcement of good taste to the act of flossing to thereby provide real time positive reinforcement to the user.

It is yet another object of the present invention to provide a dental article to a simple majority of the United States population so that they can be free of the painful "tourniquet" of the wraparound the middle fingers of conventionally available floss.

It is still another object of the present invention to provide a dental article that provides visible guidance and a target to the user for training and/or flossing purposes.

It is a further object of the present invention to provide a dental (floss training and/or flossing) article or candied article which can be easily manufactured.

An additional object of this invention is the provision of a planar dental floss that bears engaged dissolvable substrates which may be shaped in the form of cartoons, geometric figures, logos, or bear indicia thereon.

Further objects of the invention will be brought out in the following part of the specification, wherein detailed description is for the purpose of fully disclosing the invention without placing limitations thereon.

DETAILED DESCRIPTION OF THE PREFERRED EMBODIMENTS OF THE INVENTION

Figure 1:
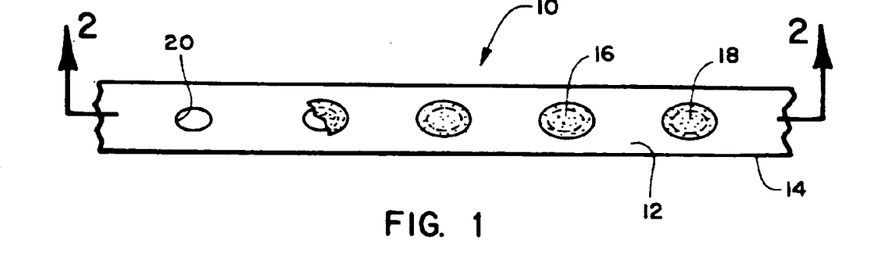
FIG. 1 is a top view of the flossing substrate showing one of the two sides of the edible film substrate overlapping the elliptical apertures in the flossing substrate.
Figure 2:
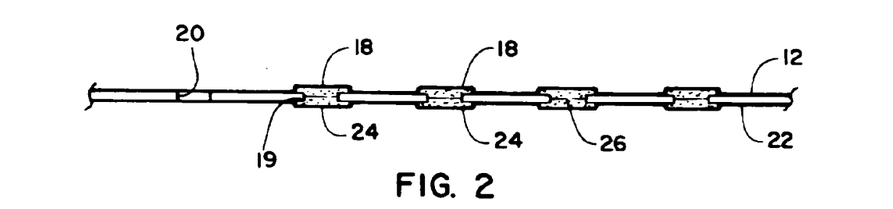
FIG. 2 shows a view through section 2-2 showing the two edible substrate sections joined through the aperture formed in the flossing substrate.
Figure 3:
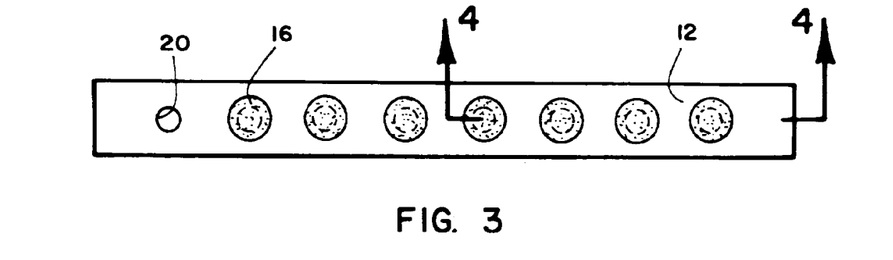
FIG. 3 depicts another favored embodiment of the device employing round apertures with overlapping edible film substrates joined therethrough.
Figure 4:
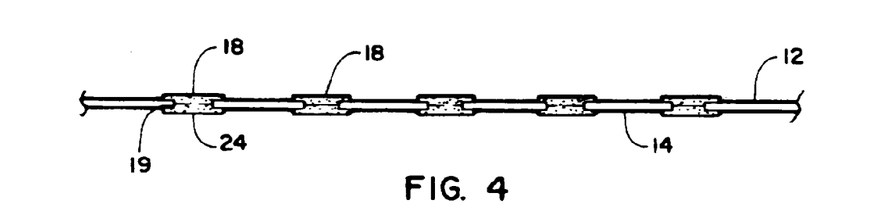
FIG. 4 is a side view through section 4-4 depicting the two edible substrate side sections joined to each other through the circular aperture.

Referring now to the drawings, FIGS. 1-13, FIG. 1 is a top view of the flossing substrate device 10 herein disclosed showing a first surface 12 of the flossing substrate 14 and the first side portion 16 of the two sides making up the edible substrate 18 material. As noted, at least one and preferably a plurality of apertures 20 are formed in the flossing substrate 14 and communicate between the first surface 12 and the second surface 22 of the flossing substrate 14. A preferred shape for the apertures 20 is that of an ellipse as shown in FIG. 1 however a circle as shown in FIG. 3 or other shapes suitable to the purpose can be used and are anticipated. The apertures 20 would be formed at a desired spacing with one current spacing being substantially four inches.

Any edible substrate 18 that is both edible and dissolves when exposed to liquid, especially saliva, may be used and formed into the first side portion 16 and second side portion 24 which are joined at their respective center portions 26 and mate through the aperture 20 to hold them both in place on the flossing substrate 14. Also, the material composing the edible substrate can have one or a combination of other ingredients to induce the user such as mouthwash, breath freshener, medicine, or flavorings. As noted above, in cases where making the edible film 18 stick to the tooth 28 during the dissolving period is desirable, a means to increase the dissolving period and adherence of the edible film 18 to the tooth 28 such as gelatin can be added to the edible substrate 18 to help it adhere to the tooth 28. Currently a mixture of 50% gelatin by weight is preferred; however those skilled in the art will realize that other mixtures may be used as well as other additives that will yield a means to increase the dissolving period and increase the adherence of the edible film 18, and all are anticipated by this application.

The first side portion 16 and second side portion 24 of the edible substrate 18 are first cut or formed to the appropriate size and shape for engagement to each other through the apertures 20. Once formed to the appropriate shape, design, and/or bearing the desired indicia or logo, the first side portion 16 and second side portion 24 are joined together, at their center sections 26, through the aperture 20 using a means to engage the first side portion 16 of edible substrate 18 to the second side portion 24. Such a means to engage can be any means to attach the first side portion 16 to the second side portion 24 at their respective center sections 26 which currently preferably includes edible adhesive, or wetting the two portions and bringing them into a sticky contact that is allowed to dry and adhere to each other, or other means to engage one side portion to the other.

The individual apertures 20 each are formed in the flossing substrate 14 with an aperture circumference which is dimensioned slightly smaller than the area of a pair of edible substrates 18 which are placed in registered engagement over the individual apertures 20. The two portions of edible substrate 18 are engaged only to each other through the planar flossing substrate 14 since they are joined to each other through the aperture 20. Both portions of the edible substrate 18 have respective perimeters slightly larger than the perimeter of the aperture 20 in-between them when they are joined. Since the two portions of the edible substrate 18 are not adhered or glued to the flossing substrate 14 itself but are engaged therethrough, there are removable easily under tension or after a defined period in the mouth dissolves the bond holding them together. In cases where tension is used to dismount the edible substrate 18, the aperture is shaped to disengage its perimeter from the sandwiched relationship between the two portions of the edible substrate 18 when they are joined. An ellipse shape has been found to be especially adept at providing this mounting release when tensioned around a tooth. Further aid in dismounting the edible substrate 18 is provided if the material forming it dissolves in saliva as noted above.

In all embodiments of the device 10, as long as portions of the circumference of both portions of the edible substrate 18 are slightly larger than the circumference of the aperture 20 through which they are joined, or one dimension of both joined portions of the edible substrate 18 is dimensioned to at least overhang opposing sides of the aperture 20, the edible substrate 18 will stay mounted in position through the flossing substrate 18. Use will dislodge the edible substrate 18 by one or a combination of tensioning of the flossing substrate 18 to stretch or deform the aperture 29 and dismount the edible substrate 18 or by dissolving of at least one of the side portions 24 to a size where it loses its overlap of the edge of the aperture 20.

Figure 5:
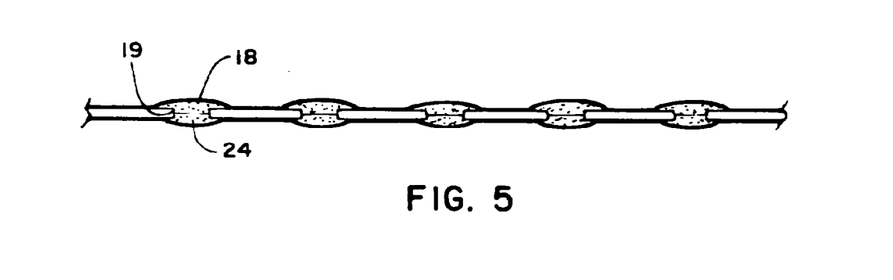
FIG. 5 depicts another embodiment of the disclosed device where the edible substrate side sections are of different diameters which could be formed in one piece and inserted in the aperture.
Figure 6:
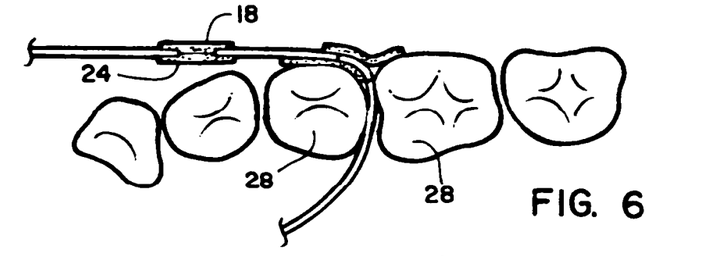
FIG. 6 depicts the edible substrate side section detaching as the flossing substrate is tensioned around a tooth.
Figure 7:
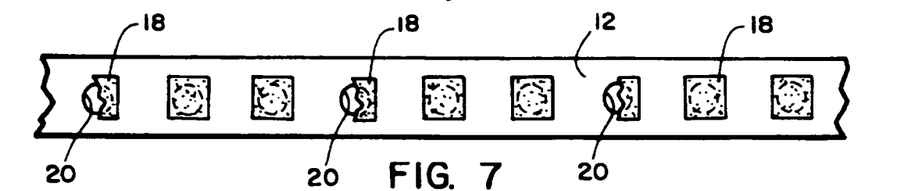
FIG. 7 shows rectangular edible substrate side sections joining through round apertures in the flossing substrate.
Figure 8:
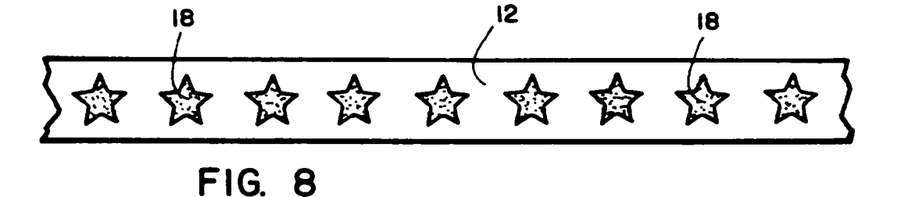
FIG. 8 shows at least one of the edible substrate side sections being shaped like a star or other geometric shape.
Figure 9:
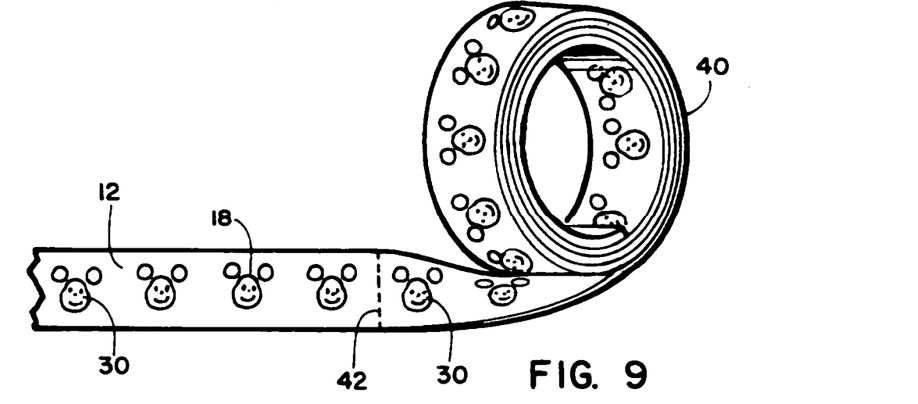
FIG. 9 depicts at least one of the edible substrate side sections being in the shape of a cartoon character and shows the material supplied in a roll optionally in frangible sections.
Figure 10:
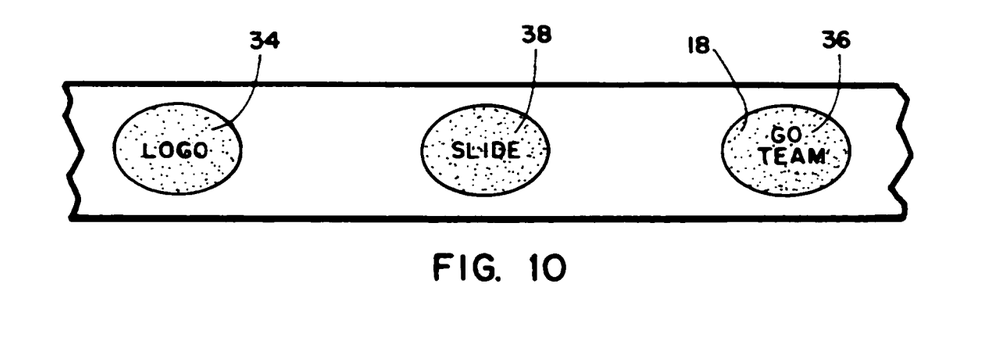
FIG. 10 depicts at least one of the edible substrate side bearing a design which can be in the shape of a logo or other design and/or bear indicia.

As noted above, the shape of the edible substrate side portions do not necessarily have to mirror that of the aperture 20 through which they are joined. Both side portions just have to have at least one side edge dimensioned to project over at least one and preferably two opposite side edges of the aperture 20 for a minimum mount in the aperture. However, dimensioning the side portions to project over the edge of the aperture 20 in two or more positions opposing each other and thereby form a recess 19 to maintain it in position in the aperture 20 yields a better mount. As shown in FIG. 5, the planar substrate formed by the two side portions may have one side portion smaller than the other so long as both overlap the aperture 20 on two opposing sides. This embodiment lends itself to the formation of the planar substrate in a single piece if desired, and insertion of the smaller side portion through the aperture 20 which in inherently flexible, wherein the aperture would retract into the recess 19 either all the way around the aperture 20 or between at least two projections from opposite sides or two projections from each side which oppose each other. However, the current preferred engagement is achieved when the dimensions of the two side portions 16 & 24 are such that at least portions of their respective substantially entire perimeters are slightly larger than the perimeter of the aperture 20. This extension defines the recess 19 in-between the two over hanging side portions 16 & 24 which in the preferred mode engages over, but does not adhere to, the flossing substrate 14 for substantially the entire perimeter of the aperture 20. However, as noted above the smaller overhanging portions, substantially less than the entire perimeter, may also be employed for the mount which may not necessarily form the recess 19 with opposing sides extending beyond the aperture 20 edge, but would impart opposing force to the two sides of the planar flossing substrate 14 to hold the engaged side portions 16 & 24 in position in the aperture 20.

The shape of the edible substrate 18 formed by the two side portions therefore can vary from simple to decorative shapes where at least one of the side portions 16 & 24 is of the desired design or ornamentation. Such designs can include but are not limited to a cartoon character 30 or geometric shape such as a star 32. The shape of the edible substrate on at least one side portion might be that of the logo 34 or could carry indicia 36 identifying the brand name of the floss 38, a sports team, or any of an infinite number of different designs, locals, or desired items to promote. In the case of indicia 36 it might be printed on one or both of the side portions 16 & 24 or engraved into them in a negative image. Dispensing of the device 10 with the edible substrate 18 in registered engagement through the apertures 20 can be provided to the user in a variety of ways such as in long rolls 40 from which sections may be removed for use using frangible sectioning 42 or, in short sections as shown in FIG. 3.

As noted earlier, the device 10 herein disclosed can also be used in combination with a method to teach and encourage proper dental flossing. In such a method the user would be provided with instructions on the proper steps and manipulation of the floss during teeth flossing. Concurrently, there would be provided the planar substrate 12 for insertion between the teeth 28. This planar substrate 12 would have at least one edible substrate 18 which would be engaged in an aperture 20 formed in the planar substrate 12. From its engagement in the aperture 20 the edible substrate 18 would be disengageable from said planar substrate 12 when said planar substrate 12 is engaged around a tooth in a correct flossing motion with correct tension to deform the aperture 20 and disengage the edible substrate 18. This would visually provide reinforcement to the user of their proper technique.

Additionally, to further encourage the use of floss, during each session, temporal coupling of a good taste or smell or treatment could be provided through the inclusion of one or a combination of mouthwash, breath freshener, medicine, or flavorings in said edible substrate 18. Additionally, positive reinforcement could be enhanced through the provision of temporally coupling of a design element to the shape of the edible substrate 18 to amuse or encourage the user at the same time the floss is being used. This design element can include one or a combination of design elements from a group of design elements consisting of a geometric shape, a cartoon shape, indicia, and a logo. The design element could also be combined with the good taste or smell noted above to provide maximum positive reinforcement to the user during a flossing or practice session.

Figure 11:
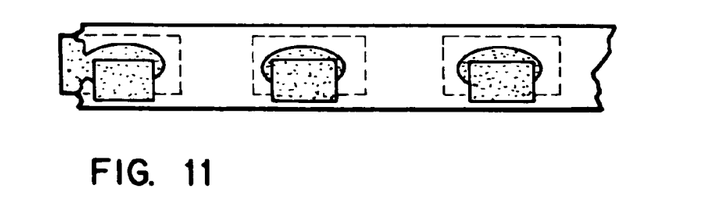
FIG. 11 shows an embodiment of the device with differing sized substrate sides engaged with one edge over the aperture.
Figure 12:
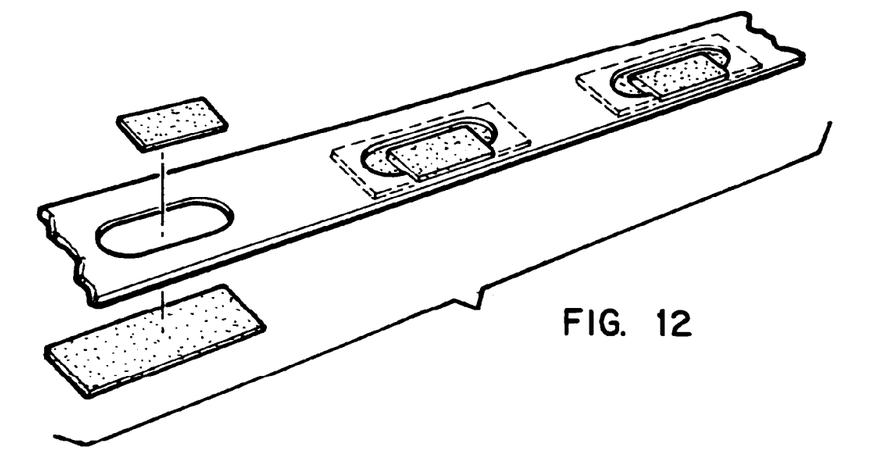
FIG. 12 shows an embodiment of the device with two different sized side sections engaged over one aperture edge.
Figure 13:
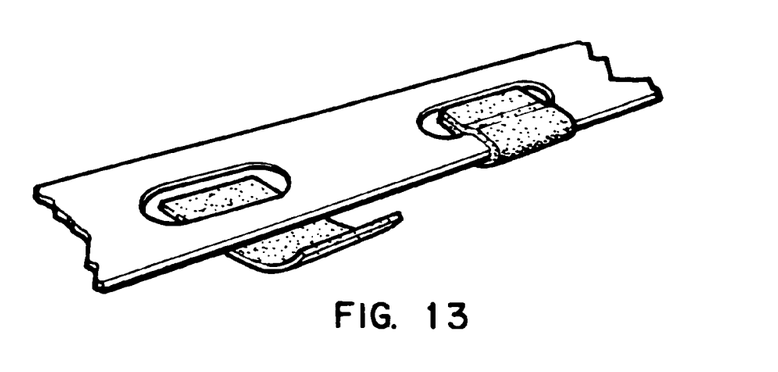
FIG. 13 depicts another embodiment of the device wherein the edible substrate engages through the aperture over a side edge where the edible substrate can be one or two pieces.

Another preferred embodiment of the device 10 is shown in FIGS. 11-13 which show the device 10 wherein the edible substrate 18 is in two pieces of different sizes with one edge engaged over the aperture on one side or with the edible substrate 18 extending around a side edge of the flossing substrate 14 to engages with itself through the aperture 20. The means for engagement of the edible substrate would be the same as noted above. The embodiment in FIG. 13 would only require a single sheet to form the edible substrate 18 or could be formed of two sheets engaged on two side edges.

While all of the fundamental characteristics and features of the present method and apparatus of the disclosed invention have been described herein, with reference to particular embodiments thereof, a latitude of modification, various changes and substitutions are intended in the foregoing disclosure and it will be apparent that in some instance, some features of the invention will be employed without a corresponding use of other features without departing from the scope of the invention as set forth. It should be understood that any such substitutions, modifications, and variations may be made by those skilled in the art without departing from the spirit or scope of the invention. Consequently, all such modifications and variations are included within the scope of the invention as defined by the following claims.

What is claimed is:

1. A dental floss apparatus comprising:

a flexible planar substrate having a first surface and a second surface;

at least one aperture formed in said planar substrate communicating between said first surface and said second surface;

at least one first side portion formed of edible substrate having a top side, and bottom side, and a perimeter edge, said first side portion positioned on said first surface over said aperture;

said perimeter of said first side portion dimensioned to form a first lip portion extending over at least one side edge of said aperture;

at least one second side portion formed of edible substrate having a top side, and bottom side, and a perimeter edge, said second side portion positioned on said second surface over said aperture;

said perimeter of said second side portion dimensioned to form a second lip portion extending over said at least one side edge of said aperture;

means to engage said bottom side of said first portion to said bottom side of said second portion to each other through said aperture thereby forming an engaged edible substrate component;

said first lip portion and said second lip portion, extending over said side edge thereby forming a recess, said recess providing a removable engagement of said side edge of said planar substrate to said edible substrate component; and said aperture deformable during a tensioning of said planar substrate around a tooth thereby providing a release of said side edge from said recess resulting in a dislodgement of said edible substrate component, from said planar substrate, into the mouth of a user.

2. The dental floss apparatus of claim 1 additionally comprising:
said engaged edible substrate dissolvable by saliva.

3. The dental floss apparatus of claim 1 additionally comprising:
said aperture being ellipse shaped.

4. The dental floss apparatus of claim 1 additionally comprising:
at least one of said first side portion or said second side portion having a design element;
said design element viewable in said mouth of said user for a duration of time subsequent to said dislodgement of said edible substrate; and
said design element including one or a combination of design elements from a group of design elements consisting of a geometric shape, a cartoon shape, indicia, and a logo.

5. The dental floss apparatus of claim 4 additionally comprising:
at least one of said first side portion or said second side portion formed of material containing one or a combination of mouthwash, breath freshener, medicine, or flavorings.

6. The dental floss apparatus of claim 1 wherein substrate is provided in fixed lengths.

7. The dental floss apparatus of claim 6 wherein,
said planar substrate is in a roll; and
said planar substrate includes a plurality of frangible portions at predetermined spacing from each other whereby said fixed lengths may be removed from said roll by tearing said frangible portions.

8. The dental floss apparatus of claim 6 additionally comprising:
at least one of said first side portion or said second side portion formed of material containing one or a combination of mouthwash, breath freshener, medicine, or flavorings.

9. The dental floss apparatus of claim 1 additionally comprising:
at least one of said first side portion or said second side portion formed of material containing one or a combination of mouthwash, breath freshener, medicine, or flavorings.

10. The dental floss apparatus of claim 2 additionally comprising:
at least one of said first side portion or said second side portion formed of material containing one or a combination of mouthwash, breath freshener, medicine, or flavorings.

11. A dental floss apparatus comprising:
a flexible planar substrate having a first surface and a second surface;
at least one aperture defined by a side edge, said aperture formed in said planar substrate said aperture communicating between said first surface and said second surface;
at least one first side portion formed of edible substrate having a top side, and bottom side, and a perimeter edge, said first side portion positioned on said first surface over said aperture;
at least one second side portion formed of edible substrate, said second side portion joined to said first side portion through said aperture to form an edible substrate component, said second side portion having a top side, and bottom side, and a perimeter edge, said second side portion positioned on said second surface over said aperture; and
said perimeter of said first side portion dimensioned to cover said at least two opposing portions of said side edge defining said aperture and said perimeter of said second side portion dimensioned to cover said at least two opposing side edges of said aperture in a recess, said recess formed between said first side portion and said second side portion;
said side edges positioned in said recess providing removable means for engagement of said edible substrate component; and
said aperture being deformable during a tensioning of said planar substrate around a tooth thereby providing means to release said edible substrate component into a mouth of a user.

12. The dental floss apparatus of claim 11 additionally comprising:
said perimeter of said first side portion is dimensioned to overhang substantially all of said edge wall defining said aperture and said perimeter of said second side portion is dimensioned to overhang substantially all of said edge wall of said aperture thereby sandwiching said planar substrate adjacent to said perimeter of said aperture in said recess therebetween.

13. The dental floss apparatus of claim 12 additionally comprising said planar substrate is a unitary structure.

14. The dental floss apparatus of claim 11 additionally comprising said planar substrate is a unitary structure.

15. The dental floss apparatus of claim 12 wherein said first side portion and said second side portion are separate structures; and
means to engage said first side portion to said second side portion.

16. The dental floss apparatus of claim 11 wherein said planar substrate is provided in fixed lengths.

17. The dental floss apparatus of claim 16 wherein
said planar substrate is in a roll; and
said planar substrate includes a plurality of frangible portions at predetermined spacing from each other whereby said fixed lengths may be removed from said roll by tearing said frangible portions.

18. A method of encouraging a person to use dental floss, comprising:
providing instructions on the proper steps in teeth flossing; and
providing a planar substrate for flossing, said planar substrate having at least one edible substrate engaged in an aperture therethrough, said edible substrate disengageable from said planar substrate and into the mouth of a user, by a deformation of said aperture during a tensioning of said planar substrate around a tooth in a correct flossing motion.

19. The method of encouraging a person to use dental floss, of claim 18 additionally comprising:

temporally coupling positive reinforcement to the user during flossing through the inclusion of one or a combination of mouthwash, breath freshener, medicine, or flavorings in said edible substrate.

20. The method of encouraging a person to use dental floss, of claim 18 additionally comprising:

temporally coupling a element to the shape of said edible substrate, said design element including one or a combination of design elements from a group of design elements consisting of a geometric shape, a cartoon shape, indicia, and a logo.

* * * * *

UNITED STATES PATENT AND TRADEMARK OFFICE
CERTIFICATE OF CORRECTION

| | | |
|---|---|---|
| PATENT NO. | : 7,281,541 B2 | Page 1 of 1 |
| APPLICATION NO. | : 10/870249 | |
| DATED | : October 16, 2007 | |
| INVENTOR(S) | : Leonard G. Lorch | |

It is certified that error appears in the above-identified patent and that said Letters Patent is hereby corrected as shown below:

Col. 14, line 3, after "a" insert -- design --.

Signed and Sealed this

Twenty Second Day of April, 2008

JON W. DUDAS
*Director of the United States Patent and Trademark Office*